United States Patent
Wang (10) Patent No.: US 7,282,042 B2
(45) Date of Patent: Oct. 16, 2007

(54) SAFETY SYRINGE

(76) Inventor: Xiping Wang, No.2, Suojiafen, Haidian District, Beijing 100088 (CN)

( * ) Notice: Subject to any disclaimer, the term of this patent is extended or adjusted under 35 U.S.C. 154(b) by 0 days.

(21) Appl. No.: 10/553,749

(22) PCT Filed: Apr. 14, 2004

(86) PCT No.: PCT/CN2004/000350

§ 371 (c)(1),
(2), (4) Date: Oct. 18, 2005

(87) PCT Pub. No.: WO2004/091698

PCT Pub. Date: Oct. 28, 2004

(65) Prior Publication Data

US 2006/0211985 A1     Sep. 21, 2006

(30) Foreign Application Priority Data

Apr. 18, 2003   (CN) ............................ 03 2 45260
Feb. 10, 2004   (CN) ..................... 2004 1 0395572

(51) Int. Cl.
   *A61M 5/00*  (2006.01)
   *A61M 5/32*  (2006.01)
(52) U.S. Cl. .................... 604/110; 604/198
(58) Field of Classification Search ........ 604/192–198, 604/263, 110, 181, 187; 128/919
   See application file for complete search history.

(56) References Cited

U.S. PATENT DOCUMENTS 4,919,652 A * 4/1990 Alter et al. ................ 604/110
5,376,080 A   12/1994 Petrussa
5,385,551 A * 1/1995 Shaw ......................... 604/110
6,626,864 B2 * 9/2003 Jansen et al. .............. 604/110

FOREIGN PATENT DOCUMENTS

| CN | 2151756 | 1/1994 |
|---|---|---|
| CN | 1092325 | 9/1994 |
| CN | 1391959 | 1/2003 |
| GB | 2243552 | 11/1991 |

* cited by examiner

*Primary Examiner*—Matthew DeSanto
(74) *Attorney, Agent, or Firm*—Rabin & Berdo, P.C.

(57) ABSTRACT

A safety syringe has a simple structure, is convenient to use, and has a low cost. The safety syringe includes a sliding casing, a needle, a syringe barrel, a piston, a latching casing, a spring and a plunger inside the syringe barrel. The safety syringe can be easily used to carry out an injection and has a safety mechanism that can be actuated using a single hand. The sliding casing can be automatically positioned and locked in two directions. This design guarantees that, during processing of the syringe after it is used, the needle's point is always protected by the sliding casing. The safey syringe is also auto-locking; after it has been used, the plunger is locked in the syringe barrel and cannot be pulled out any longer. Any attempt to use the syringe again will cause the plunger to be broken and the syringe to be damaged, thus ensuring a one-time use.

16 Claims, 5 Drawing Sheets

FIG 12

US 7,282,042 B2

SAFETY SYRINGE

This application is a 371 of PCT/CN04/00350 filed on Apr. 14, 2004, which claims priority benefits from China patent application numbers CN 03245260.8 filed Apr. 18, 2003 and CN 100395572.7 filed Feb. 10, 2004.

BACKGROUND OF THE INVENTION

1. Technical field

The present invention relates to a safety syringe, particularly to an auto-disable safety syringe of needle-protective functionality.

2. Background of the Art

At present, more and more diseases are contaminated through blood, bodily fluid, etc. One of main channels that cause disease to spread is using the same syringe for multiple times and inappropriately handling the needle of a syringe after it is used. However, commonly used disposable syringes may occasionally prick medical staffs after injection or hurt the workers processing medical waste later, thereby existing considerable latent safety problems. Although there have been many domestic or international patents in relation to disposable safety syringes, most of the syringes may not be widely adopted due to complicated configuration, high cost for manufacturing, inconvenience for use and functional inadequacy.

The patent of invention of filing No. 94101555.6 disclosed a disposable safety syringe, including a protective casing, which is moveably sleeved on the outside of a syringe barrel to make itself be able to move from an inactivated contracted position to a safety position in the front. Where it is at the inactivated contracted position, a needle protrudes from the protective casing, which has a fixation device to automatically retain the protective casing at the safety position in the front so that the protective casing cannot contract with respect to the syringe barrel. Such an invention can protect the needle, yet it has the following problems:

First, the overall configuration of the invention is complicated; thereby making its dies possess complex structures that shorten the service life of the dies. As a result, the investment on manufacture and cost goes up.

The second, the invention comprises many parts, which raise the difficulty of assembly process as well as production cost.

The third, the invention only carries out a protection for the needle. Yet no auto-latching and auto-disable functions regarding to the whole syringe are implemented. Therefore, some other parts (e.g. plunger) that might be taken off to reuse are still latent safety problems to patients.

The fourth, the invention reserves a defined space at the front end of the syringe, thereby bringing a considerable inconvenience for some applications of the syringe, e.g. blood withdrawal.

SUMMARY

The present invention aims to provide a safety syringe of a simple structure at low cost, which can be used conveniently. The safety syringe does not only have needle-protective functionality and is also auto-disable.

To implement a syringe that meets the aforementioned aims, the present invention adopts the following technical schemes. The safety syringe comprises a sliding casing, a needle, a syringe barrel, a piston, a spring and a plunger provided inside the syringe barrel, at the front end of which a luer tip with a needle luer skirt thereon to engage with the needle and is provided; the needle is installed on the luer tip at the front end of the syringe barrel through the needle luer skirt; a connection head is provided at the front end of the plunger to attach to the piston; the syringe is characterized in that the sliding casing is moveably sleeved on the outside of the syringe barrel, two elastic extension plates are provided at the rear end of the sliding casing, on each of the elastic extension plates a respective connection part is provided; At least one short groove is formed in the middle of the sliding casing; Two elastic locking plates are provided at the short groove; Also, a reduced section is formed at the front end of the sliding casing; In the middle of a guard board that is provided at the front end of the reduced section, a hole permitting the needle to protrude is formed; A vertical ringy face is provided at the front end of the syringe barrel; A long groove engaging with the elastic locking plates is formed on the surface of the syringe barrel; At the front portion of the long groove, a position limiting plate is provided; The position limiting plate can be locked between the two elastic locking plates; Two connecting portions are formed on the surface of the syringe barrel respectively corresponding to the connection parts on the elastic extension plates so that the connecting portions can respectively fit and connect with the connection parts on the elastic extension plates; A off-locking plate is provided to the plunger to correspond to the elastic extension plates of the sliding casing; In the opposite planes of the off-locking plate and the elastic extension plates of the sliding casing at least one is a slant face; When the off-locking plate and the elastic extension plates of the sliding casing contact with each other, the off-locking plate may make the elastic extension plates of the sliding casing opening towards its two sides under the action of the slant face; The spring is sleeved on the outer casing of the needle luer skirt of the syringe barrel and compressed between the guard board of the sliding casing and the vertical ringy face of the syringe barrel.

In the above safety syringe, the rear portion of the syringe barrel is provided with at least two resistance rings. Furthermore, the syringe also includes a latching casing whose front end is a tapered face contracted inward and is provided with at least two long grooves. In addition, a locking ring is formed at the central portion of the surface of the latching casing. The latching casing is installed at the rear portion of the inner hole of the syringe barrel and is sleeved on the plunger. The main body of the plunger is a "+" (across) shaped rib plate including a front "+" shaped rib plate, a middle "+" shaped rib plate, a stepped resistance plate and a rear "+" shaped rib plate. The outline size of the front "+" shaped rib plate is slightly larger than the inner diameter of the front end of the latching casing, the outline size of the middle "+" shaped rib plate is smaller than the diameter of the inner hole at the front end of the latching casing, the number of the stepped resistance plate is at least one, and the outer diameter thereof is slightly larger than the diameter of the inner hole at the front end of the latching casing.

In the aforementioned safety syringe, a front resistance ring of a triangular cross-section and a rear resistance ring of a trapezoid-shaped cross-section are provided at the rear portion of the inner hole of the syringe barrel. The front resistance ring has a triangular cross-section and the inner diameter thereof is slightly smaller than the inner diameter of the syringe barrel. The angle between the frontal slant face of the front resistance ring and the axis of the syringe barrel is small, whereas the angle between the rear slant face of the front resistance ring and the axis of the syringe barrel is large. The rear resistance ring has a trapezoid-shaped cross-section; the angle between its frontal slant face and the axis of the syringe barrel and the angle between its rear slant face and the axis of the syringe barrel are both large. The inner diameter of the rear resistance ring is smaller than that of the front resistance ring. The front end face of the locking ring of the latching casing is perpendicular to the axis of the syringe barrel, and the angle between the rear slant face thereof and the axis of the syringe barrel is large. The outer diameter of the locking ring is equal to the inner diameter of the syringe barrel. The width of the locking ring is slightly smaller than the distance between the front resistance ring and the rear resistance ring in the syringe barrel. The distance between the front end face of the locking ring of the latching casing and the rear slant face of the front resistance ring is slightly larger the distance between the front end face of the latching casing and the rear end face of the stepped resistance plate.

In the aforementioned safety syringe, the connection part may be a locking notch formed on the elastic extension plate, the connecting portion is a protruding platform provided on the syringe barrel to correspond to the locking notch. The protruding platform can be locked in the locking notch.

In the aforementioned safety syringe, the connection part of the elastic extension plate may be a "T" shaped plate. The rear end of the syringe barrel is provided with a protruding ring. The connecting portion is a groove formed on the protruding ring to engage with the "T" shaped plate so that the "T" shaped plate can be locked in the groove.

In the aforementioned safety syringe, the connection part of the elastic extension plate may be a bark-shaped plate. The connecting portion of the syringe barrel is the rear end face of the syringe barrel and the bark-shaped plate can be is locked on the rear end face of the syringe barrel.

In the aforementioned safety syringe, two long grooves, where individual elastic extension plate is further provided respectively, are formed at the rear portion of the sliding casing. The connection parts on the elastic extension plates are the locking notches respectively formed on the elastic extension plates. The connecting portions are protruding platforms provided on the syringe barrel to respectively correspond to each locking notch. The protruding platforms can be locked in the corresponding locking notches.

In the above safety syringe, the diameter of the inner hole of the piston is larger than the diameter of the connecting portion of the head of the plunger, the length of the piston is 1~5 mm larger than the thickness of the connecting portion of the plunger.

In the above safety syringe, a circular anti-pull-off plate is provided on the "+" shaped rib plate of the plunger from where the distance to the rear stepped plate is equal to the distance from the front end face of the latching casing to the rear end face of the locking ring. The outer diameter of the circular anti-pull-off plate is slightly smaller than the diameter of the inner hole at the rear end of the latching casing.

In the above safety syringe, a weak connecting area is provided on the rear "+" shaped rib plate. Its two horizontal rib plates are connected by two small breakable connecting pillars, which are respectively symmetric with its centers; while its two vertical rib plates are connected by a breakable narrow belt.

In the above safety syringe, a transitional slant face or a transitional tapered platform is between the front "+" shaped rib plate and the rear "+" shaped rib plate of the plunger. The angle between the slant face and the axis is not less than 30 degrees.

In the above safety syringe, the end portions of the two elastic locking plates at the short groove of the sliding casing protrude towards the inner hole, the protruding height is slightly larger than the depth of the long grooves in the syringe barrel. The height of the protruding platform of the syringe barrel is smaller than the depth of the locking notch. The width of the protruding platform is smaller than that of the locking notch.

The present invention has the following advantages over the prior arts by adopting the above designs;

The present invention can be easily used to carry out an injection and to initiate its safety mechanism by a single hand. The sliding casing can be automatically positioned and locked in two directions, this design guarantees during processing the syringe after it is used, the pinhead is always protected by the sliding casing, thereby avoiding such an occurrence that the pinhead may hurt the operators;

Also, the present invention has a reliable function of auto-locking; therefore, once the syringe is used, the plunger has been locked in the syringe barrel and cannot be pulled out any longer, any attempt to use the syringe again will cause the plunger broken and the syringe damaged, thus ensuring a one-time use.

The piston of the present invention can be assembled optimally. Not only the structure of the invention is simplified to make operation convenient (the invention is fully equal to common syringes with respect to injection operation), the invention is but also designed to meet the requirements to control the accuracy of used dosage for injection, to guarantee the operational safety of blood withdrawal, and to make the variation of pushing force of injection negligible so that the easiness of injection is not affected essentially. Furthermore, initiating the safety mechanism (to make sliding casing moved forward) will not be started until injection is finished, therefore it does not affect the patients negatively.

The present invention has a simplified structure considering the medical fluid in the syringe. The parts of syringe that contact with the medical fluid are only the syringe barrel and the piston (fully equal to common syringes), thereby reliably avoiding the medical fluid to be contaminated and guaranteeing the safety of injection.

The present invention makes a change of standard needle easy so that it satisfies the different requirements of use.

The structures of the parts of the present invention is relatively concise among the like safety syringes, so it is convenient for manufacturing and easy for assembling, thus leading to a high cost effectiveness.

The present invention can make the automatic or semi-automatic assembly easily realized, thereby creating a better condition for mass production.

BRIEF DESCRIPTION OF THE DRAWINGS

The accompanying figures, which are incorporated in and constitute a part of the specification, illustrating presently preferred embodiments of the invention. Together with the above general description and the following detailed description, the figures serve to explain the principles of the invention.

DETAILED DESCRIPTION

Figure 1:
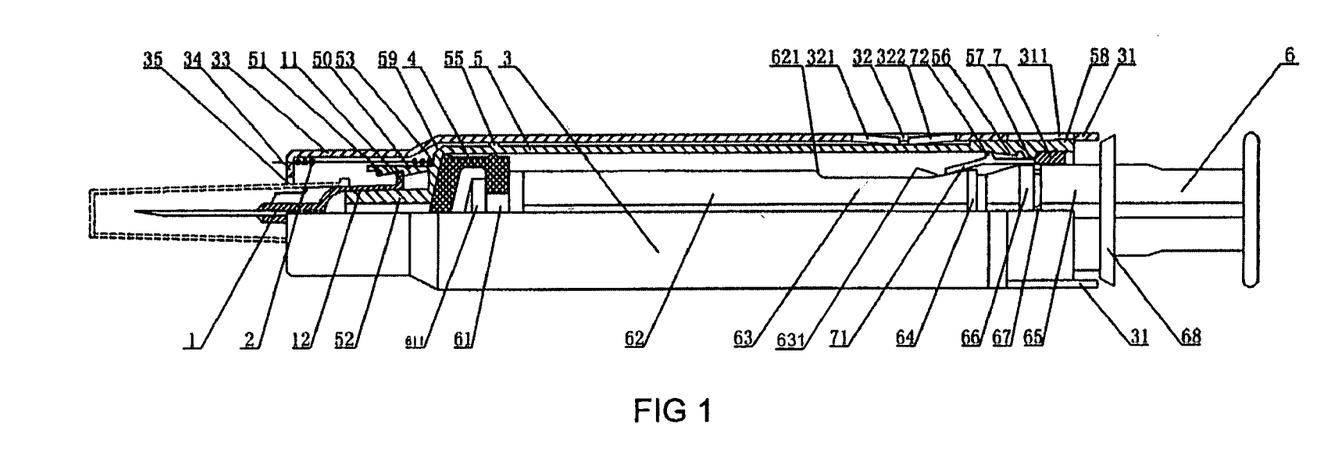
FIG. 1 is a schematic view of the configuration of the present invention.
Figure 2:
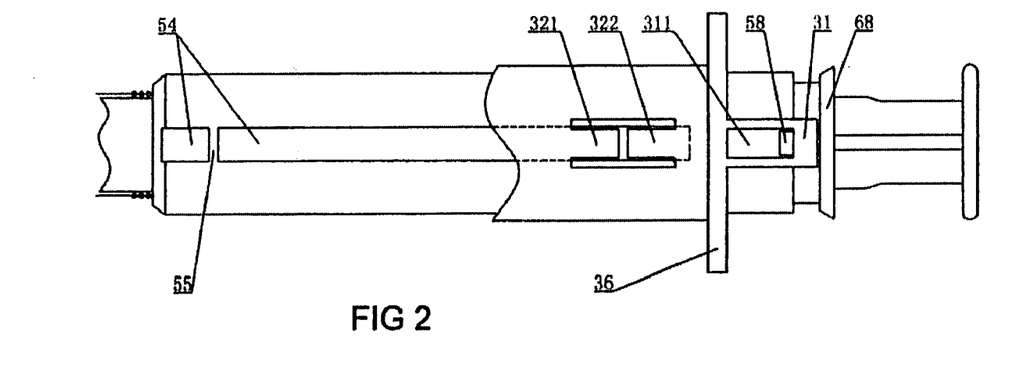
FIG. 2 is a top view of the FIG. 1.

FIG. 1 and FIG. 2 show a schematic view of the configuration of an embodiment according to the present invention, namely a safety syringe in an unused state after its assembly. The syringe comprises a needle 1, a spring 2, a sliding casing 3, a piston 4, a syringe barrel 5, a plunger 6 and a latching casing 7.

The injection needle 1 may be engaged with a needle luer skirt 51 at the front end of the syringe barrel 5 by screwing the flange 11 on the needle base so that the inner hole 12 of the needle base engages with a luer tip 52 of the syringe barrel.

The sliding casing 3 is moveably sleeved on the outside of the syringe barrel 5. The rear portion of the sliding casing 3 is provided with two elastic extension plates 31, on each of which a connection part is respectively provided. In this embodiment, the connection part is a locking notch 311 respectively grooved on each of the extension plates 31. The middle portion of the sliding casing has two short grooves 32, on each of which an elastic locking plate 321 and an elastic locking plate 322 are respectively provided. The front end of the sliding casing 3 is a reduced section 33, at the front of which a guard board 34 is provided and a hole 35 permitting the needle to reach out is provided in the center of the guard board 34.

A vertical ringy face 53 is provided in the front end of the syringe barrel 5, on whose surface two long grooves 54 are provided for engaging with the elastic locking plates 321 and 322 respectively. A respective position limiting plate 55 is provided at the front end of each long groove 54. The end portion of each elastic locking plate 321 or 322 protrudes toward the inner hole, the protruding length is slightly larger than the depth of the long groove 54 in the syringe barrel so that the end portion of the elastic locking plate 321 or 322 can respectively slide in the long grooves 54. Furthermore, the position limiting plate 55 can be locked between the elastic locking plates 321 and 322.

The rear portion of the inner side of the syringe barrel 5 is provided with two resistance rings 56 and 57. The cross section of the front resistance ring 56 is a triangular and its inner diameter is slightly smaller than the inner diameter of the syringe barrel 5. The front slant face of the front resistance ring 56 holds a 10-degree angle with respect to the axis and its rear slant face is perpendicular to the axis. The cross section of the rear resistance ring 57 is a trapezoid and both its front slant face and its rear slant face has a 45-degree angle with respect to the axis of the syringe barrel. The inner diameter of the rear resistance ring 57 is smaller than the inner diameter of the front resistance ring 56. A connecting portion is respectively provided on the outside of the syringe barrel 5 to correspond to the connection part of the elastic extension plate 31. In this embodiment, the connecting portion is provided on a protruding platform 58 on the rear portion of the syringe barrel 5 to correspondingly engage with the locking notch 311 of the elastic extension 31. The height of the protruding platform 58 is smaller than the depth of the locking notch 311 and the width of the protruding platform 58 is smaller than the width of the locking notch 311. Furthermore, the protruding platform 58 can be locked in the locking notch 311. In addition, a transitional tapered plane is provided between the vertical ringy face 52 and the surface of the syringe barrel 5 with a view to easily assembling.

The latching casing 7 is installed at the rear portion of the inner hole of the syringe barrel 5 and sleeved on the plunger 6. The front portion of the latching casing 7 is a hollowed tapered elastic plate 71 contracted inward and has three or four long grooves in it. A locking ring 72 is provided on the surface in the middle part of the latching casing 7. The perpendicular axis of the front end face of the locking ring 72 and the rear slant face thereof form a 45-degree angle with the axis respectively. The outer diameter of the locking ring 72 is equal to the diameter of the inner hole of the syringe barrel 5. The width of the locking ring 72 is slightly smaller than the width between the front resistance ring 56 and the rear resistance ring 57 inside the syringe barrel.

The "+" shaped rib plate of the plunger 6 is formed into several sections with different structures and sizes, namely, a front "+" shaped rib plate 62, a middle "+" shaped rib plate 63, a stepped resistance plate 64 and a rear "+" shaped rib plate 65. The front "+" shaped rib plate 62 has an outline size that is slightly larger than the diameter of the inner hole at the front end of the latching casing, while the middle "+" shaped rib plate 63 has an outline size that is smaller than the diameter of the inner hole at the front end of the latching casing. Between the front "+" shaped rib plate 62 and the middle "+" shaped rib plate is a transitional slant face 621 (or a tapered plane), which holds a 45-degree angle with respect to the axis. Also, between the uniquely provided stepped resistance plate 64 and the middle "+" shaped rib plate 63 is another transitional slant face 631, which holds a 15-degree angle with respect to the axis. A circular anti-pull-off plate 66 whose outer diameter is slightly smaller than the diameter of the inner hole at the rear end of the latching casing 7 is provided at a place on the rear "+" shaped rib plate 65 from which the distance to the stepped resistance plate 64 is equal to the distance from the front end face of the latching casing 7 to the rear end face of the locking ring 72. A weak connecting area 67 is provided on the anti-pull-off plate 66 of the rear "+" shaped rib plate 65, between the horizontal rib plates are two small breakable connecting pillars the perpendicular rib plates. A tapered off-locking plate 68 is provided on the rear "+" shaped rib plate 65 to correspond to the elastic extension plate 31 of the sliding casing 3. At least one opposite plane of the off-locking plate 68 and the elastic extension plate 31 is a slant face. When the off-locking plate 68 contacts with the elastic extension plate 31 of the sliding casing, the off-locking plate 68 affected by the slant face may make the elastic extension plate 31 slightly opening towards its two sides. In this embodiment, the end face of the elastic extension plate 31 is perpendicular to the axis, while the off-locking plate is a tapered plate whose small end diameter is smaller than the inner diameter of the sliding casing 3 and whose large end diameter is larger than the inner diameter of the sliding casing 3.

The same result that the off-locking plate 68 pushes the elastic extension plate 31 to open towards its two sides may be also obtained by letting the end face of the elastic extension plate 31 be a slant face and the off-locking plate 68 be a cylindrical plate. Therefore, each of the two designs mentioned above falls into the scope of protection under the present invention.

The spring 2 is sleeved on an outer casing 50 of the needle luer shirt of the syringe barrel and is compressed between the guard board 34 of the sliding casing and the vertical ringy face 53 of the syringe barrel. Since the spring 2 is defined by the inner hole of the reduced section 33 of the sliding casing and is held by the surface plane of the outer casing 50 of the needle luer shirt at the front end of the syringe barrel, the spring cannot be distorted laterally and affected regarding the elasticity.

The diameter of the inner hole of the piston 4 is larger than the diameter of the connection part 611 of the plunger head 61, while the length of the inner hole of the piston is larger than the thickness (4 mm) of the connection part 611 of the plunger.

Furthermore, the distance from the front end face of the locking ring 72 of the latching casing 7 to the rear slant face of the front resistance ring 56 should slightly larger than the distance from the front end face of the latching casing 7 to the rear end face of the stepped resistance plate 64.

Figure 3:
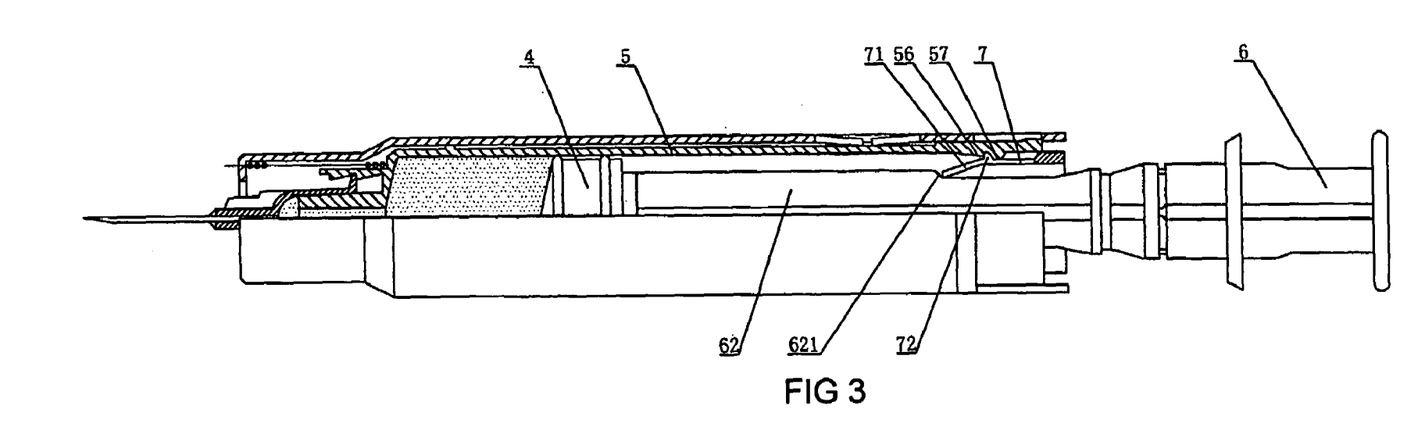
FIG. 3 is a schematic view of the configuration of the present invention when the fluid is withdrawn.

FIG. 3 shows the situation when syringe is being used. A fluid-withdrawal (or blood-withdrawal) can be realized by letting the plunger 6 to move back, which in turn brings the piston 4 to move, thereby forming a vacuum inside the front portion of the syringe barrel. When the plunger is pulled to the extent that the transitional slant face of the plunger touches the front end face of the latching casing, the plunger brings the latching casing 7 to move back along the front slant face of the front resistance ring 56. Since the height of the front resistance ring 56 is small, the angle of the front slant face thereof is very small, the angle of the transitional slant face 621 of the plunger is large, the latching casing 7 can overcome a resistance from the front resistance ring 56 and slide back. However, when the locking ring 72 on the latching casing 7 slips into between the front resistance ring 56 and the rear resistance ring 57 of the syringe barrel, because the inner diameter of the rear resistance ring 57 is small and the angle between its front slant face and the axis is large, the increased resistance makes the latching casing 7 not move back any longer. The front portion of the latching casing 7 has a great elasticity, therefore, the front elastic plate 71 can distort under the action of the transitional slant face 621 and move across the transitional slant face 621 of the plunger until it slides to the surface of the front "+" shaped rib plate 62 before the plunger so that the fluid-withdrawal (or blood-withdrawal) can be continued until the operational process is finished. It is clear that the syringe utilizes a necessary pull-back action on the plunger to realize the functional positioning of the latching casing 7; furthermore, since the rear end face of the front resistance ring 56 is perpendicular to the axis and the front end face of the locking ring 72 on the latching casing 7 is also perpendicular to the axis, the latching casing 7 having realized the functional positioning can not move back and forth any longer.

Figure 4:
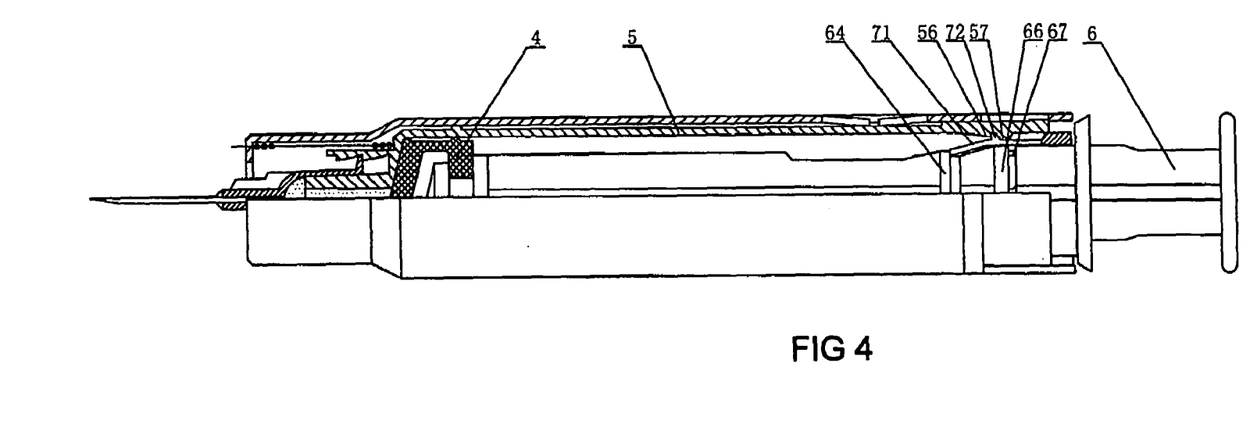
FIG. 4 is a schematic view of the configuration of the present invention after the injection is finished.

FIG. 4 show that the embodiment functions the same as common syringes in an operational process of pushing a medical fluid. The plunger 6 pushes the piston 4 to move forward inside the syringe barrel so that the medical fluid therein can be injected into a human body through the syringe barrel 5 and the needle 1; Consequently, the front end face of the latching casing 7 is moved back, the stepped resistance plate 64 on the plunger 6 goes through the inner hole of the elastic plate 71 at the front end of the latching casing; Since the frontal elastic plate 71 of the latching casing 7 has a good elasticity, the resistance received by the plunger 6 is relatively low, thereby causing the pushing force of the injection insignificantly changed; Put it another way, no uncomfortable feeling is accompanied during the injection; When the front end face of the piston 4 is reached to the front wall of the inner hole of the syringe barrel, the injection is finished. As a result, the plunger 6 is defined inside the syringe barrel 5 by the latching casing 7 and cannot be pulled out again. If the plunger 6 is withdrawn, the rear end face of the stepped resistance plate 64 thereon may touch the front end face of the latching casing 7. Because both the two end faces are perpendicular to the axis, a great resistance can be generated. However, the size of the anti-pull-off plate 66 of the plunger 6 is similar to that of the inner hole of the latching casing 7, thereby avoiding the locking ring 72 on the latching casing to detach from the front resistance ring 56 and the rear resistance ring 57 due to its contracting movement inward. If the pulling force is further increased, the plunger 6 may break at the connecting pillars on the horizontal rib plate in the weak connecting area 67 or at the thin connecting belt and damage, thereby avoiding a reuse of the syringe (as in FIG. 5).

Figures 5, 6:
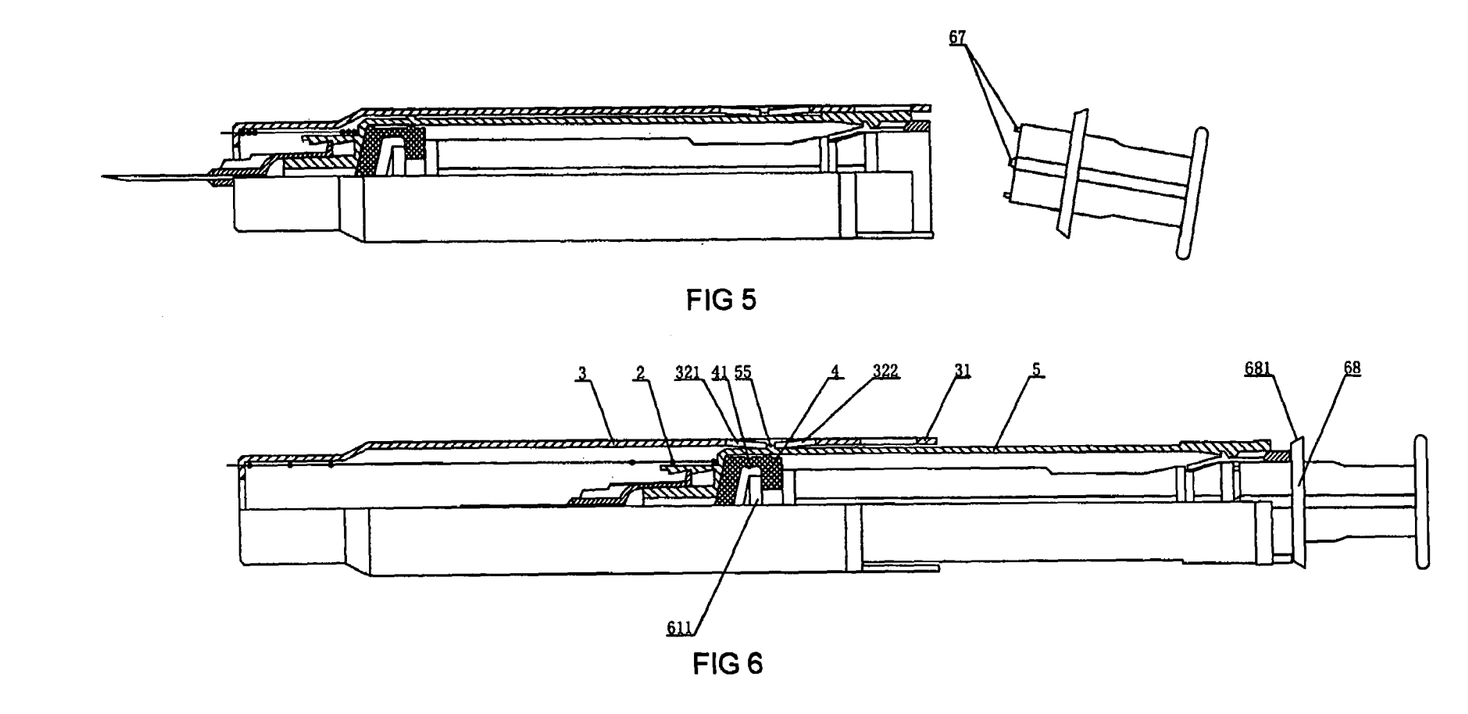
FIG. 5 is a schematic view of the configuration of the present invention when it is pulled broken.
FIG. 6 is a schematic view of the configuration of the present invention that carries out the functionality of a needle.

The FIG. 6 shows that in a normal operation, if the plunger 6 is further pushed forward a little after the injection (or the syringe is withdrawn from the patient's body), the transitional cylinder 41 of the piston can be compressed because the thickness of the connection part 61 of the plunger is smaller than the length of the inner hole of the piston 4; Put it another way, the plunger 6 can keep moving forward for about 1 to 3 mm; Also, because the off-locking plate 68 on the plunger 6 is close to or in contact with the end portion of the elastic extension plate 31 of the sliding casing after the injection, when the plunger is further moved forward, the slant face 681 on the plunger may touch the end portion of the elastic extension plate 31 to push the extension plate 31 move outward; As a result, the end face of the locking notch 311 in contact with the end face of the protruding platform 58 of the syringe barrel is also moved outward; When the amount of the movement is larger than the height of the protruding platform, the sliding casing 3 and the syringe barrel 5 may slide with respect to each other under the action of the spring 2; Due to the sliding distance which is larger than the length of a section of the needle protruding from the front end of the sliding casing 3, the pinhead 11 of the needle 1 is covered inside the sliding casing 3, thereby avoiding the pinhead to hurt people and realizing the safety protection function for the syringe needle. Obviously, at this moment, the front elastic locking plate 321 of the sliding casing has crossed over the position limiting plate 55 on the syringe barrel (because the distance between the two elastic locking plates is larger than the thickness of the position limiting plate 55) and is on the left of the front end face of the position limiting plate 55 so as to stop the sliding casing to move backward, thereby defining the sliding casing 3 at a position shown in the FIG. 6 and realizing a reliable safety functionality.

In addition, as shown in the figures, the wing plate 36 is installed on the sliding casing 3; that means an index finger and a middle finger of an operator are respectively placed at each side of the wing plate 36. Therefore, once the sliding casing 3 and the syringe barrel 5 give a relative movement, it is the truth that the syringe barrel 5 is moved backward and is pulled into the sliding casing 3 together with the needle 1. Such a configuration has advantages that if the safety mechanism is initiated so that the needle can be automatically pulled out from the human body, while the sliding casing does not move forward to touch human body and does not bring patients painful or uncomfortable. It is obvious that installing the wing plate 36 on the syringe barrel 5 is another feasible structure.

Figure 7:
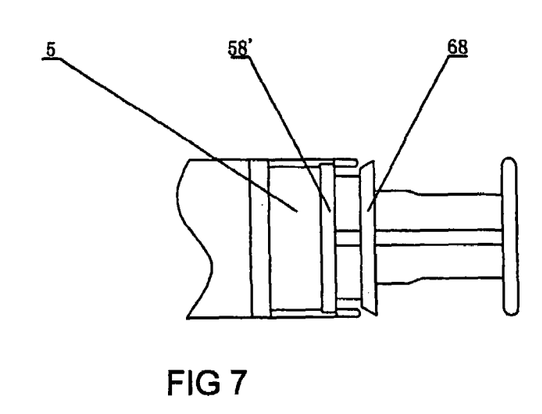
FIG. 7 is a schematic view of the configuration of another embodiment of the present invention.
Figure 8:
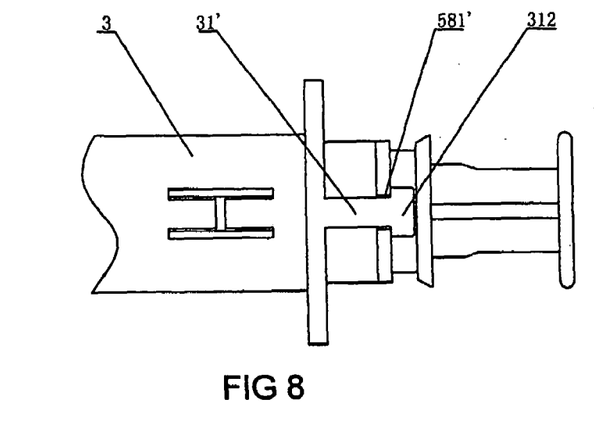
FIG. 8 is a top view of the FIG. 7.

FIG. 7 and FIG. 8 show a schematic view of the configuration of another embodiment of the present invention. Its main changes compared to the embodiment provided from FIG. 1 to FIG. 6 include that the connection part of the elastic extension plate of the sliding casing 3 is a "T" shaped plate 31'; a protruding ring 58' is provided at the rear end of the syringe barrel 5; the connecting portion on the syringe barrel is a groove 581' formed on the protruding ring 58' to engage with the "T" shaped plate 31'; and the "T" shaped plate 31' can be locked in the groove 581'. After the syringe is used, the off-locking plate 68 similarly pushes the end face of the elastic extension plate so that the elastic extension plate is slightly opened outward, thereby making a "T" shaped head 312 detach with from the groove 581'; As a result, the sliding casing 3 and the syringe barrel 5 have a sliding movement with respect to each other under the action of the spring 2, causing the needle to be protected.

Figure 9:
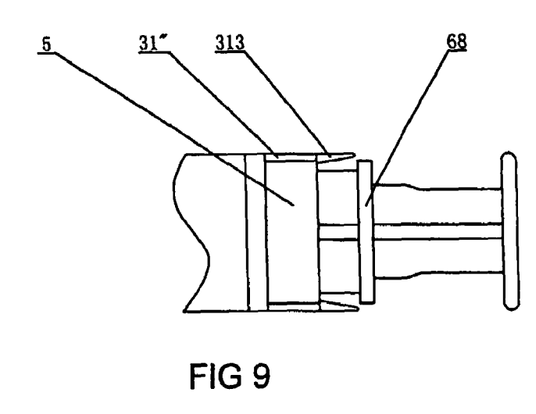
FIG. 9 is a schematic view of the configuration of still another embodiment of the present invention.
Figure 10:
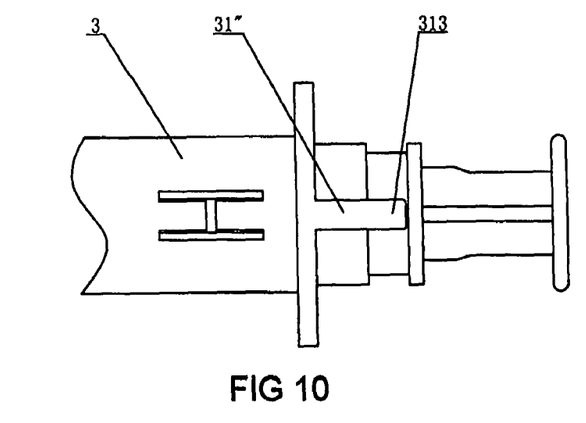
FIG. 10 is a top view of the FIG. 9.

Further, FIG. 9 and FIG. 10 show a schematic view of the configuration of still another embodiment of the present invention. Its main changes compared to the embodiment provided from FIG. 1 to FIG. 6 include the connection part of the elastic extension plate of the sliding casing 3 is a bark-shaped plate 31", which may be bark-fixed on the rear end face of the syringe barrel 5. After the syringe is used, the off-locking plate 68 similarly pushes the end face of the elastic extension plate so that the elastic extension plate is slightly opened outward, thereby making the bark 313 of the elastic extension plate unhooked from the rear end face of the syringe barrel 5; As a result, the sliding casing 3 and the syringe barrel 5 have a sliding movement with respect to each other under the action of the spring 2, causing the needle to be protected.

Figure 11:
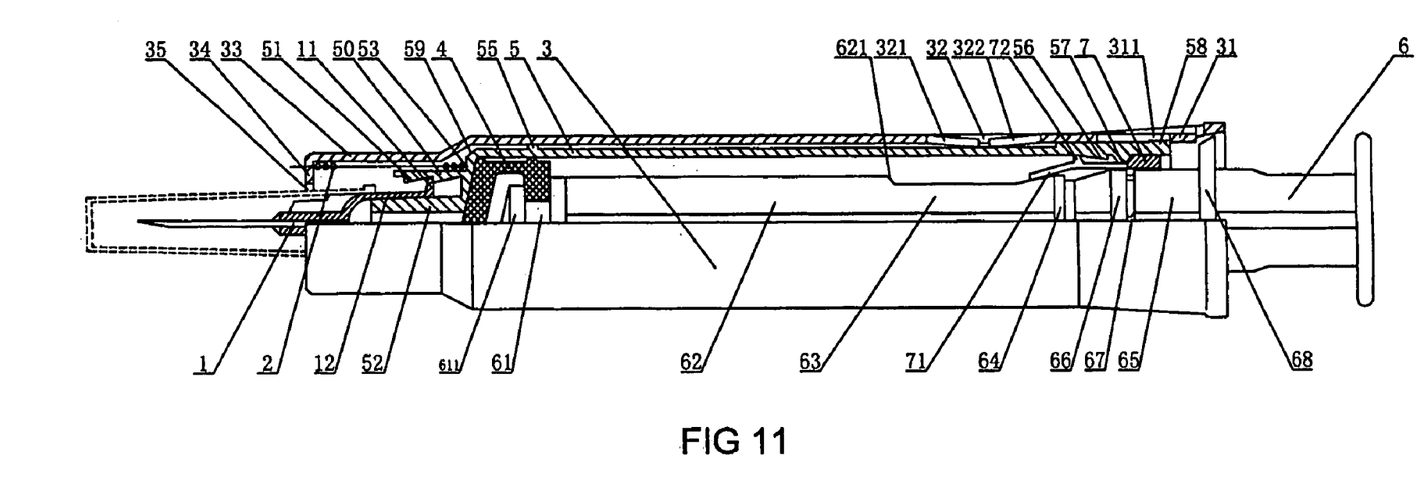
FIG. 11 is a schematic view of the configuration of still another embodiment of the present invention.
Figure 12:
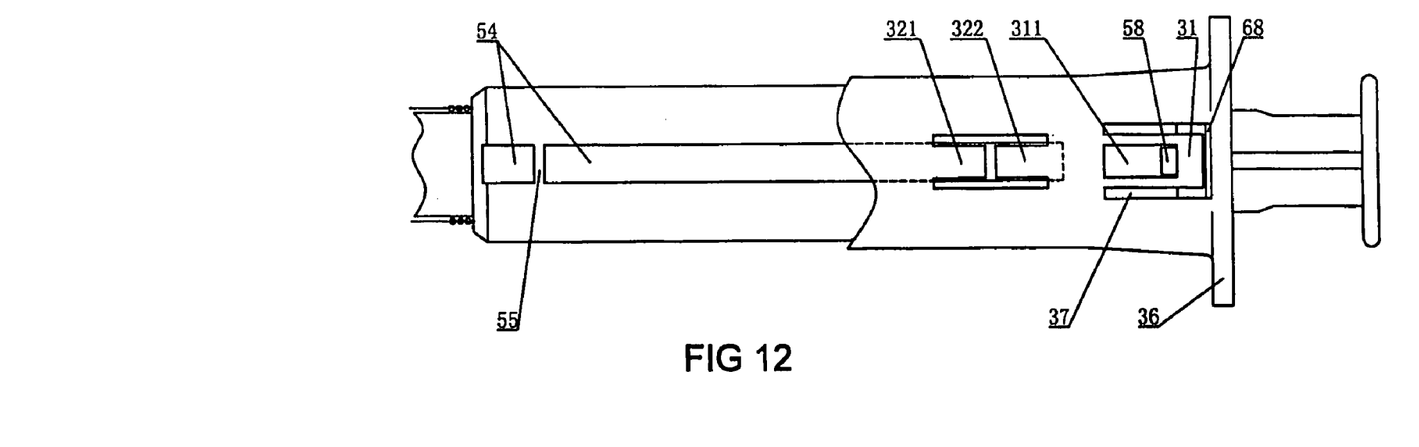
FIG. 12 is a top view of the FIG. 11.

Furthermore, FIG. 11 and FIG. 12 show a schematic view of the configuration of still another embodiment of the present invention. Its main changes compared to the embodiment provided from FIG. 1 to FIG. 6 include two grooves 37 formed on the rear portion of the sliding casing 3; a respective elastic extension plate 31 is provided at two grooves 37; The respective connection part on each elastic extension plate 31 is the a locking groove 311 formed on the elastic extension plate; a connecting portion is a protruding platform 58 provided on the syringe barrel 5 to engage with the locking groove 311; and the protruding platform 58 can be locked in the locking groove 311.

INDUSTRIAL APPLICABILITY

The present invention can be easily used to carry out an injection and to initiate its safety mechanism by a single hand. The sliding casing can be automatically positioned and locked in two directions. This design guarantees during processing the syringe after it is used, the pinhead is always protected by the sliding casing, thereby avoiding such an occurrence that the pinhead may hurt the operators; Also, the present invention has a reliable function of auto-locking, therefore, once the syringe is used, the plunger has been locked in the syringe barrel and cannot be pulled out any longer; any attempt to use the syringe again will cause the plunger broken and the syringe damaged, thus ensuring a one-time use. Among the like safety syringes, the invention has a concise configuration for parts, which is convenient for manufacturing and is easy for assembling, therefore the invention has significant features such as high performance and low cost. Furthermore, the configuration of the present invention can easily realize automatic or semi-automatic assembly, which creates a good condition for mass production.

I claim:

1. A safety syringe including a sliding casing, a needle, a syringe barrel, a piston, a spring, and a plunger inside the syringe barrel; a luer tip with a needle luer skirt thereon provided at the front end of the syringe barrel to mate with the needle that is installed on the luer tip at the front end of the syringe barrel through the needle luer skirt, with the front end of the plunger having a connection part to engage with the piston, is characterized in that:

the sliding casing is moveably sleeved on the outside of the syringe barrel, with two elastic extension plates on each of which a connection part is respectively being provided at the rear portion of the sliding casing; the front end of the sliding casing is a reduced section whose front end has a guard board whose center is provided with a hole permitting the needle to reach out;

a vertical ringy face is provided at the front end of the syringe barrel whose surface has a long groove to engage with elastic locking plates, the front portion of the long groove is provided with a position limiting plate that can be locked between the two elastic locking plates; the outside surface of the syringe barrel is provided with two connecting portions to respectively correspond to the connection part of each elastic extension plate, the connecting portions can engage with the connection parts on the elastic extension plates respectively;

the plunger is provided with a sliding casing off-locking plate corresponding to the elastic extension plate of the sliding casing, at least one opposite face of the sliding casing off-locking plate and the elastic extension plate of the sliding casing is a slant face; when the sliding casing off-locking plate and the elastic extension plate of the sliding casing is in contact with each other, the sliding casing off-locking plate may make the said elastic extension plate of the sliding casing opening toward its two sides under the action of the slant face;

the spring is sleeved on the casing of the needle luer skirt of the syringe barrel and is compressed between the guard board of the sliding casing and the vertical ringy face of the syringe barrel;

wherein the syringe barrel is provided with at least two resistance rings at its rear portion; the syringe further includes a latching casing whose front portion is a tapered plane contracted inward with at least two long grooves thereon and whose surface is provided with a locking ring in the central section; the latching casing is installed at the rear portion of an inner hole of the syringe barrel and is sleeved on the plunger;

the main body of the plunger is a "+" shaped rib plate including a front "+" shaped rib plate, a middle "+" shaped rib plate, a stepped resistance plate and a rear "+" shaped rib plate; the outline size of the front "+" shaped rib plate is slightly larger than the diameter of the inner hole at the front end of the latching casing, the outline size of the middle "+" shaped rib plate is smaller than the diameter of the inner hole at the front end of the latching casing, the number of the stepped resistance plate whose outer diameter is slightly larger than the diameter of the inner hole at the front end of the latching casing is at least one; and wherein the rear portion of the inner hole of the syringe barrel has a front resistance ring with a triangular cross section and a rear resistance ring with a trapezoid-shaped cross section; the cross section of the front resistance ring is triangular and its inner diameter is slightly smaller than the inner diameter of the syringe barrel, the angle between the front slant face of the front resistance ring and the axis is small, the angle between the rear slant face and the axis is large; the cross section of the rear resistance ring is trapezoid-shaped, the front slant face and the rear slant face of the rear resistance ring respectively hold a large angle with respect to the axis of the syringe barrel, the inner diameter of the rear resistance ring is smaller than the inner diameter of the front resistance ring; the front end face of the locking ring of the latching casing is perpendicular to the axis, the angle between the rear slant face and the axis is large, the outer diameter of the locking ring equals to the diameter of the inner hole of the syringe barrel, the width of the locking ring is slightly smaller than the width between the front resistance ring and the rear resistance ring inside the syringe barrel; the distance from the front end face of the locking ring of the latching casing to the rear slant face of the front resistance ring is slightly larger than the distance from the front end face of the latching casing to the rear end face of the stepped resistance plate of the plunger.

2. The safety syringe according to claim 1, wherein the connection part is the locking notch formed on the elastic extension plate, the connecting portion is a protruding platform provided on the syringe barrel to correspond to the locking notch, the protruding platform can be locked in the locking notch.

3. The safety syringe according to claim 2, wherein the rear portion of the sliding casing is provided with two grooves, the two grooves are respectively provided with the elastic extension plate, the connection part on the elastic extension plate is the locking notch provided on the elastic extension plate, the connecting portion is a protruding platform provided on the syringe barrel to correspond to the locking notch in which the protruding platform can be locked.

4. The safety syringe according to claim 3, wherein the diameter of the inner hole of the piston is larger than the diameter of the connection part of the head of the plunger and the length of the inner hole is 1 to 5 mm larger than the thickness of the head of the plunger.

5. The safety syringe according to claim 4, wherein the rear "+" shaped rib plate of the plunger is provided with a circular anti-pull-off plate from which the distance to the rear stepped plate is equal to the distance from the front end face of the latching lock casing to the rear end face of the locking ring, and the outer diameter of the circular anti-pull-off plate is slightly smaller than the diameter of the inner hole at the rear end of the latching casing.

6. The safety syringe according to claim 5, wherein the respective end portion of two elastic locking plates at the short groove of the sliding casing protrudes toward the inner hole and the protruding height is slightly larger than the depth of the long groove in the syringe barrel; the height of the protruding platform is not smaller than the depth of the locking notch and the width of the protruding platform is smaller than the width of the locking notch.

7. The safety syringe according to claim 3, wherein the rear "+" shaped rib plate of the plunger is provided with a circular anti-pull-off plate from which the distance to the rear stepped plate is equal to the distance from the front end face of the latching lock casing to the rear end face of the locking ring, and the outer diameter of the circular anti-pull-off plate is slightly smaller than the diameter of the inner hole at the rear end of the latching casing.

8. The safety syringe according to claim 3, wherein the respective end portion of two elastic locking plates at the short groove of the sliding casing protrudes toward the inner hole and the protruding height is slightly larger than the depth of the long groove in the syringe barrel; the height of the protruding platform is not smaller than the depth of the locking notch and the width of the protruding platform is smaller than the width of the locking notch.

9. The safety syringe according to claim 2, wherein the connection part of the elastic extension plate is a bark-shaped plate, the connecting portion of the syringe barrel is the rear end face of the syringe barrel on which the bark-shaped plate may be locked.

10. The safety syringe according to claim 9, wherein the diameter of the inner hole of the piston is larger than the diameter of the connection part of the head of the plunger and the length of the inner hole is 1 to 5 mm larger than the thickness of the head of the plunger.

11. The safety syringe according to claim 9, wherein the rear "+" shaped rib plate of the plunger is provided with a circular anti-pull-off plate from which the distance to the rear stepped plate is equal to the distance from the front end face of the latching lock casing to the rear end face of the locking ring, and the outer diameter of the circular anti-pull-off plate is slightly smaller than the diameter of the inner hole at the rear end of the latching casing.

12. The safety syringe according to claim 9, wherein the respective end portion of two elastic locking plates at the short groove of the sliding casing protrudes toward the inner hole and the protruding height is slightly larger than the depth of the long groove in the syringe barrel; the height of the protruding platform is not smaller than the depth of the locking notch and the width of the protruding platform is smaller than the width of the locking notch.

13. The safety syringe according to claim 2, wherein the connection part of the elastic extension plate is a "T" shaped plate, a protruding ring is provided at the rear end of the syringe barrel, the connecting portion is a groove formed on the protruding ring to engage with the "T" shaped plate, the "T" shaped plate can be locked in the groove.

14. The safety syringe according to claim 2, wherein the diameter of the inner hole of the piston is larger than the diameter of the connection part of the head of the plunger and the length of the inner hole is 1 to 5 mm larger than the thickness of the head of the plunger.

15. The safety syringe according to claim 2, wherein the rear "+" shaped rib plate of the plunger is provided with a circular anti-pull-off plate from which the distance to the rear stepped plate is equal to the distance from the front end face of the latching lock casing to the rear end face of the locking ring, and the outer diameter of the circular anti-pull-off plate is slightly smaller than the diameter of the inner hole at the rear end of the latching casing.

16. The safety syringe according to claim 2, wherein the respective end portion of two elastic locking plates at the short groove of the sliding casing protrudes toward the inner hole and the protruding height is slightly larger than the depth of the long groove in the syringe barrel; the height of the protruding platform is not smaller than the depth of the locking notch and the width of the protruding platform is smaller than the width of the locking notch.

* * * * *